United States Patent
Odermatt et al.

(10) Patent No.: US 9,456,765 B2
(45) Date of Patent: Oct. 4, 2016

(54) SYSTEMS AND METHODS FOR MEASURING PARAMETERS IN JOINT REPLACEMENT SURGERY

(71) Applicant: MAKO Surgical Corp., Ft. Lauderdale, FL (US)

(72) Inventors: Daniel Odermatt, Ft. Lauderdale, FL (US); Matthew Thompson, Durham, NC (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 0 days.

(21) Appl. No.: 14/863,115

(22) Filed: Sep. 23, 2015

(65) Prior Publication Data

US 2016/0008087 A1    Jan. 14, 2016

Related U.S. Application Data

(62) Division of application No. 13/234,190, filed on Sep. 16, 2011, now Pat. No. 9,167,989.

(51) Int. Cl.
*A61B 19/00* (2006.01)
*A61B 5/06* (2006.01)
(Continued)

(52) U.S. Cl.
CPC .................. *A61B 5/06* (2013.01); *A61B 5/107* (2013.01); *A61B 5/4528* (2013.01); *A61B 5/4571* (2013.01); *A61B 5/4851* (2013.01); *A61B 34/20* (2016.02); *G06F 19/3437* (2013.01); *A61B 2505/05* (2013.01)

(58) Field of Classification Search
CPC ............ A61B 19/50; A61B 2019/501; A61B 2019/502; A61B 2019/504; A61B 2019/507; A61B 5/107; A61B 5/4528; A61B 5/4571; A61B 5/4851

USPC ..... 606/86 R–89 R, 102; 600/424, 587, 595; 623/22.11–23.38
See application file for complete search history.

(56) References Cited

U.S. PATENT DOCUMENTS

| | | | | |
|---|---|---|---|---|
| 4,841,975 A | * | 6/1989 | Woolson | A61B 17/154 378/205 |
| 4,936,862 A | * | 6/1990 | Walker | A61F 2/30942 128/898 |
| 5,871,018 A | * | 2/1999 | Delp | A61B 17/154 128/898 |

(Continued)

FOREIGN PATENT DOCUMENTS

| | | | |
|---|---|---|---|
| GB | WO 2009106812 A1 | * | 9/2009 |
| WO | WO-2009/106812 | | 9/2009 |

*Primary Examiner* — Christian Sevilla
*Assistant Examiner* — Eric S Gibson
(74) *Attorney, Agent, or Firm* — Foley & Lardner LLP

(57) ABSTRACT

A computer-assisted surgery system includes a display, an input device configured to receive data input by a user, and a processor, coupled to the input device and the display. The processor is configured to establish a first position of a pre-operative center of rotation of a joint in a first coordinate space of a first bone and a second coordinate space of a second bone and establish a second position of the pre-operative center of rotation of the joint in the first coordinate space, wherein the second position is a projection into the first coordinate space of the position of the pre-operative center of rotation maintained in a constant position in the second coordinate space. The processor is further configured to determine a change in a parameter associated with the joint based on the first and second positions and output a result indicating the determined change to the display.

16 Claims, 10 Drawing Sheets

(51) Int. Cl.
    *A61B 5/107* (2006.01)
    *A61B 5/00* (2006.01)
    *G06F 19/00* (2011.01)

(56) References Cited

U.S. PATENT DOCUMENTS

| | | | | |
|---|---|---|---|---|
| 5,920,395 | A * | 7/1999 | Schulz | A61B 5/0064 356/141.1 |
| 5,995,738 | A * | 11/1999 | DiGioia, III | A61B 17/15 623/914 |
| 6,245,109 | B1 * | 6/2001 | Mendes | A61B 5/06 623/18.11 |
| 6,447,448 | B1 * | 9/2002 | Ishikawa | A61B 5/0031 128/899 |
| 6,662,036 | B2 * | 12/2003 | Cosman | A61B 6/5247 600/411 |
| 6,711,431 | B2 * | 3/2004 | Sarin | A61B 5/103 600/426 |
| 6,711,432 | B1 * | 3/2004 | Krause | A61B 17/15 128/922 |
| 7,033,360 | B2 * | 4/2006 | Cinquin | A61B 5/107 128/920 |
| 7,060,102 | B2 * | 6/2006 | Thompson | A61F 2/3609 623/23.35 |
| 7,383,164 | B2 * | 6/2008 | Aram | A61F 2/30942 600/300 |
| 7,606,613 | B2 * | 10/2009 | Simon | A61B 6/463 600/414 |
| 7,611,541 | B2 * | 11/2009 | Thompson | A61F 2/3609 623/23.35 |
| 7,618,419 | B2 * | 11/2009 | Lavallee | A61B 90/36 600/437 |
| 7,769,429 | B2 * | 8/2010 | Hu | A61B 5/103 600/424 |
| 7,885,705 | B2 | 2/2011 | Murphy | |
| 7,955,280 | B2 | 6/2011 | Radinsky et al. | |
| 8,010,180 | B2 * | 8/2011 | Quaid | A61B 17/1764 600/424 |
| 8,014,984 | B2 * | 9/2011 | Iannotti | A61F 2/30942 623/19.13 |
| 8,034,057 | B2 | 10/2011 | Penenberg | |
| 8,257,360 | B2 * | 9/2012 | Richard | 606/102 |
| 8,439,926 | B2 * | 5/2013 | Bojarski | A61B 17/17 606/88 |
| 8,444,651 | B2 * | 5/2013 | Kunz | A61B 17/175 606/87 |
| 8,480,754 | B2 * | 7/2013 | Bojarski | A61F 2/30942 606/79 |
| 8,603,180 | B2 * | 12/2013 | White | A61B 17/1666 606/91 |
| 8,617,171 | B2 * | 12/2013 | Park | B23P 17/04 606/87 |
| 8,626,267 | B2 * | 1/2014 | Lavallee | A61B 17/154 600/424 |
| 8,635,082 | B2 * | 1/2014 | Woods | G06F 19/321 705/2 |
| 8,693,634 | B2 * | 4/2014 | Ramamurthi | A61B 6/505 378/62 |
| 8,702,712 | B2 * | 4/2014 | Jordan | A61B 17/155 606/86 R |
| 8,721,721 | B2 * | 5/2014 | Linder-Ganz | A61F 2/3872 606/102 |
| 8,737,700 | B2 * | 5/2014 | Park | A61B 5/055 382/128 |
| 2003/0004518 | A1 * | 1/2003 | Perren | A61B 5/1077 606/102 |
| 2003/0225415 | A1 * | 12/2003 | Richard | A61B 90/36 606/102 |
| 2004/0092944 | A1 * | 5/2004 | Penenberg | A61F 2/3609 606/91 |
| 2004/0171924 | A1 * | 9/2004 | Mire | G06F 19/3437 600/407 |
| 2004/0181149 | A1 * | 9/2004 | Langlotz | A61B 90/36 600/431 |
| 2004/0243148 | A1 * | 12/2004 | Wasielewski | A61B 17/00 606/130 |
| 2005/0149050 | A1 * | 7/2005 | Stifter | A61B 90/36 606/102 |
| 2005/0281465 | A1 * | 12/2005 | Marquart | A61B 90/36 382/195 |
| 2006/0122541 | A1 * | 6/2006 | Tuma | A61B 5/107 600/587 |
| 2006/0264731 | A1 * | 11/2006 | Murphy | A61F 2/4657 600/407 |
| 2006/0287613 | A1 * | 12/2006 | Amiot | A61F 2/4657 600/587 |
| 2006/0293614 | A1 * | 12/2006 | Radinsky | A61B 5/103 600/587 |
| 2007/0005145 | A1 * | 1/2007 | Banks | A61B 5/6846 623/23.42 |
| 2007/0066917 | A1 * | 3/2007 | Hodorek | A61B 90/36 600/595 |
| 2007/0173815 | A1 * | 7/2007 | Murase | A61B 17/15 606/53 |
| 2007/0209220 | A1 * | 9/2007 | Murphy | A61B 5/103 33/512 |
| 2007/0249967 | A1 * | 10/2007 | Buly | A61B 5/1121 600/595 |
| 2008/0039717 | A1 * | 2/2008 | Frigg | G06F 19/3437 600/424 |
| 2008/0146969 | A1 * | 6/2008 | Kurtz | A61B 17/56 600/595 |
| 2008/0234833 | A1 * | 9/2008 | Bandoh | A61F 2/30942 623/23.15 |
| 2008/0255584 | A1 * | 10/2008 | Beverland | A61B 5/103 606/130 |
| 2008/0287781 | A1 * | 11/2008 | Revie | A61B 90/36 600/426 |
| 2008/0294258 | A1 * | 11/2008 | Revie | A61B 5/7246 623/16.11 |
| 2008/0312663 | A1 * | 12/2008 | Haimerl | G06T 7/0012 606/130 |
| 2008/0319449 | A1 * | 12/2008 | Tuma | A61B 90/36 606/102 |
| 2009/0105714 | A1 * | 4/2009 | Kozak | A61F 2/4657 606/102 |
| 2010/0030231 | A1 * | 2/2010 | Revie | A61B 90/36 606/130 |
| 2010/0081971 | A1 * | 4/2010 | Allison | G06F 19/3481 601/2 |
| 2010/0152859 | A1 * | 6/2010 | Thompson | A61F 2/3609 623/20.36 |
| 2010/0170362 | A1 | 7/2010 | Bennett et al. | |
| 2011/0013148 | A1 * | 1/2011 | Friese | 353/30 |
| 2011/0092858 | A1 * | 4/2011 | Burger | A61B 19/50 600/587 |
| 2011/0160738 | A1 * | 6/2011 | McIntosh | A61B 19/5244 606/102 |
| 2011/0264009 | A1 * | 10/2011 | Walter | A61B 5/4504 600/595 |
| 2012/0116412 | A1 * | 5/2012 | Penenberg | A61F 2/3609 606/102 |
| 2013/0053855 | A1 * | 2/2013 | Bertram, III | A61B 17/1764 606/89 |
| 2013/0072821 | A1 * | 3/2013 | Odermatt | A61B 5/06 600/595 |
| 2013/0114866 | A1 * | 5/2013 | Kasodekar | A61B 5/1071 382/128 |
| 2013/0158557 | A1 * | 6/2013 | Komistek | A61B 17/15 606/89 |
| 2013/0226190 | A1 * | 8/2013 | Mckinnon | A61F 2/46 606/102 |
| 2013/0324890 | A1 * | 12/2013 | Youssef | A61B 5/11 600/595 |
| 2013/0332128 | A1 * | 12/2013 | Miles | G06F 19/3437 703/6 |
| 2014/0188240 | A1 * | 7/2014 | Lang | A61F 2/30942 623/22.12 |
| 2014/0277542 | A1 * | 9/2014 | Stein | A61B 17/154 623/20.32 |

\* cited by examiner

SYSTEMS AND METHODS FOR MEASURING PARAMETERS IN JOINT REPLACEMENT SURGERY

CROSS-REFERENCE TO RELATED APPLICATIONS

This application is a divisional of U.S. application Ser. No. 13/234,190, filed Sep. 16, 2011, which is hereby incorporated by reference herein in its entirety.

TECHNICAL FIELD

The present disclosure relates generally to orthopedic surgery and, more particularly, to systems and methods for measuring parameters associated with joint replacement surgeries.

BACKGROUND

For most surgical procedures, it is advantageous for a surgeon to compare intra-operative progress and post-operative results with a pre-operative plan to ensure that surgical objectives are met. In some surgical procedures, particularly those involving orthopedic arthroplasty, relatively small deviations from a pre-operative plan can translate into significant differences in the functionality of the patient's anatomy. For example, in joint replacement surgery on the knee or hip, small changes in the positioning of the prosthetic joint components may result in considerable differences in the patient's posture, gait, and/or range of motion.

During orthopedic procedures involving resurfacing, replacement, or reconstruction of ball-and-socket joints, such as in the hip, surgeons attempt to ascertain differences between the pre-operative joint and the reduced, newly-implanted joint. The surgeon may analyze these differences during the surgery to evaluate the accuracy of the position of the implant and determine whether additional adjustment of the implant is required before finishing the surgery.

There are three commonly-used parameters that are used to quantify differences in prosthetic joint placement: leg length (also called hip length), offset, and anterior/posterior position. Leg length refers to the longitudinal extent of the leg measured along the superior/inferior axis relative to the pelvis. Offset refers to the position of the leg along the medial-lateral axis relative to the pelvis. Anterior/posterior ("AP") position of the leg, as the name suggests, refers to position of the leg along the anterior/posterior axis with respect to the pelvis.

Early methods for calculating leg length, offset, and anterior/posterior position required the surgeon to use rulers and gauges to perform manual measurements on the hip joint before and after attaching the prosthetic implants. Such measurements, however, are often inaccurate due to the difficulty in performing manual measurements in the surgical environment using conventional rulers and gauges. Further, manual measurements are not easily repeatable or verifiable, and can take a significant amount of time to perform.

Subsequent development of computer-assisted surgical navigation systems enabled real-time tracking of relative positions of bones and other anatomical features in a defined coordinate space. Using these systems, surgeons electronically register the position and orientation of certain anatomical landmarks, such as bones, and track the position and orientation of these landmarks relative to other defined landmarks. Conventional computer-assisted techniques for calculating leg length, offset, and anterior/posterior position in hip replacement procedures involved using these tracking capabilities to electronically measure a pre-operative position of the femur relative to the pelvis in a specific predetermined reference position. After the hip replacement prostheses are implanted and the joint is reduced, the surgeon attempts to manually return the femur according to a surgical plan. Once the surgeon believes he has positioned according to the plan, the surgeon prompts the system to determine changes in leg length, offset, and anterior/posterior position.

Although conventional computer-assisted techniques for measuring hip replacement parameters may increase the speed and precision of the measurements, their accuracy depends largely upon the accuracy with which the surgeon positioned the femur after implantation of the replacement joint. Indeed, if the surgeon fails to return the femur to the precise position and orientation, the hip parameters are subject to considerable error. In some cases, this error may lead the surgeon to conclude that an improperly-aligned prosthetic is within an acceptable threshold of planned surgical goals, and end the surgery. In other cases, an alignment error may lead the surgeon to conclude that a properly-aligned prosthetic deviates unacceptably from the threshold of planned surgical goals, causing the surgeon to make unnecessary adjustments to the position of the prosthetic implant(s) that may lead to a misalignment. In either case, the patient may experience post-operative discomfort or, in the case of a severe misalignment, a dislocation of the prosthetic femoral head from the acetabular cup. Such discomfort and/or dislocation may require corrective surgery, prolonged rehabilitation, and undue expense.

The presently disclosed systems and methods for measuring parameters in joint replacement surgery are directed to overcoming one or more of the problems set forth above and/or other problems in the art.

SUMMARY OF THE INVENTION

According to one aspect, the present disclosure is directed to a computer-implemented method for determining changes in parameters of a hip joint due to modification of the hip joint. The method may comprise estimating, by a processor associated with a computer, a first position of a pre-operative center of rotation of the joint in a first coordinate space. The method may further comprise estimating, by the processor, a second position of the pre-operative center of rotation of the joint in the first coordinate space, when the estimated pre-operative center of rotation is maintained in a constant position in a second coordinate space. The processor may then estimate a change in a parameter associated with the joint based on the first and second positions.

In accordance with another aspect, the present disclosure is directed to a method for determining changes in parameters of a hip joint after a hip arthroplasty procedure. The method may comprise estimating a first position of a center of a native femoral head of a hip joint. After modification of the hip joint, a position of a center of rotation of the modified hip joint may be estimated, and mechanical and epicondyle axes of a femur associated with the modified hip joint may be established. The method may further comprise virtually positioning the mechanical axis of the femur as substantially parallel with the superior/inferior axis of a pelvis associated with the hip joint. The method may also comprise virtually positioning the epicondyle axis of the femur as substantially parallel with the medial/lateral axis of the pelvis. A second position of the center of the native femoral head may be estimated based on the virtual positioning of the mechanical and epicondyle axes. Leg length and offset associated with the modified hip joint may be determined based on the first and second positions of the center of the native femoral head.

According to another aspect, the present disclosure is directed to another method for determining a change in a parameter associated with a joint caused by a modification of a portion of the joint, the method comprising establishing a first point of reference relative to a first bone of a joint, wherein the first point of reference is indicative of an estimated pre-operative center of rotation of the joint. After a modification of the joint, a second point of reference indicative of an estimated post-modification center of rotation of the joint may be estimated, and a virtual representation of the first bone may be positioned in a predetermined pose relative to the second point of reference. The method may further comprise approximating, based on the positioning of the virtual representation of the first bone in the predetermined pose, a third point of reference, indicative of a position of the first point of reference relative to a change in position of the first bone caused by the modification of the joint. The method may also comprise estimating a change in a parameter associated with the joint based on a difference between the third point of reference and the first point of reference.

In accordance with another aspect, the present disclosure is directed to yet another method for determining a change in a parameter of a hip joint caused by modification of a portion of the hip joint. The method comprises approximating a first position of a center of a native femoral head relative to the femur, approximating a reference point between femoral epicondyles, and approximating, after modification of the femur, a position of a center of rotation of the prosthetic joint in the pelvic space. The method may further comprise establishing a first axis associated with the modified femur, wherein the first axis comprises the approximated position of the center of the prosthetic femoral head and the approximated reference point between the femoral epicondyles. The method may also comprise establishing a second axis associated with the modified femur, wherein the second axis comprises a transverse axis through the femoral epicondyles. The first axis may be virtually positioned as substantially parallel with the superior/inferior axis of the pelvic space, and the second axis may be virtually positioned as substantially parallel with the coronal plane of the pelvic space. A second position of the center of the native femoral head in the pelvic space may be approximated based on the virtually-positioned first and second axes. The method may further include estimating, in the pelvic space, a difference between the second position of the center of the native femoral head relative to the first position of the center of the native femoral head.

According to yet another aspect, the present disclosure is directed to a computer-assisted surgery system. The computer-assisted surgery system may comprise a display, an input device configured to receive data input by a user, and a processor, operatively coupled to the input device and the display. The processor may be configured to estimate a first position of a pre-operative center of rotation of the joint in a first coordinate space. The processor may be further configured to estimate a second position of the pre-operative center of rotation of the joint in the first coordinate space, when the estimated pre-operative center of rotation is maintained in a constant position in a second coordinate space. The processor may also be configured to estimate a change in a parameter associated with the joint based on the first and second positions, and output a result, indicative of the estimated change in the parameter to the display.

DETAILED DESCRIPTION

Figure 1:
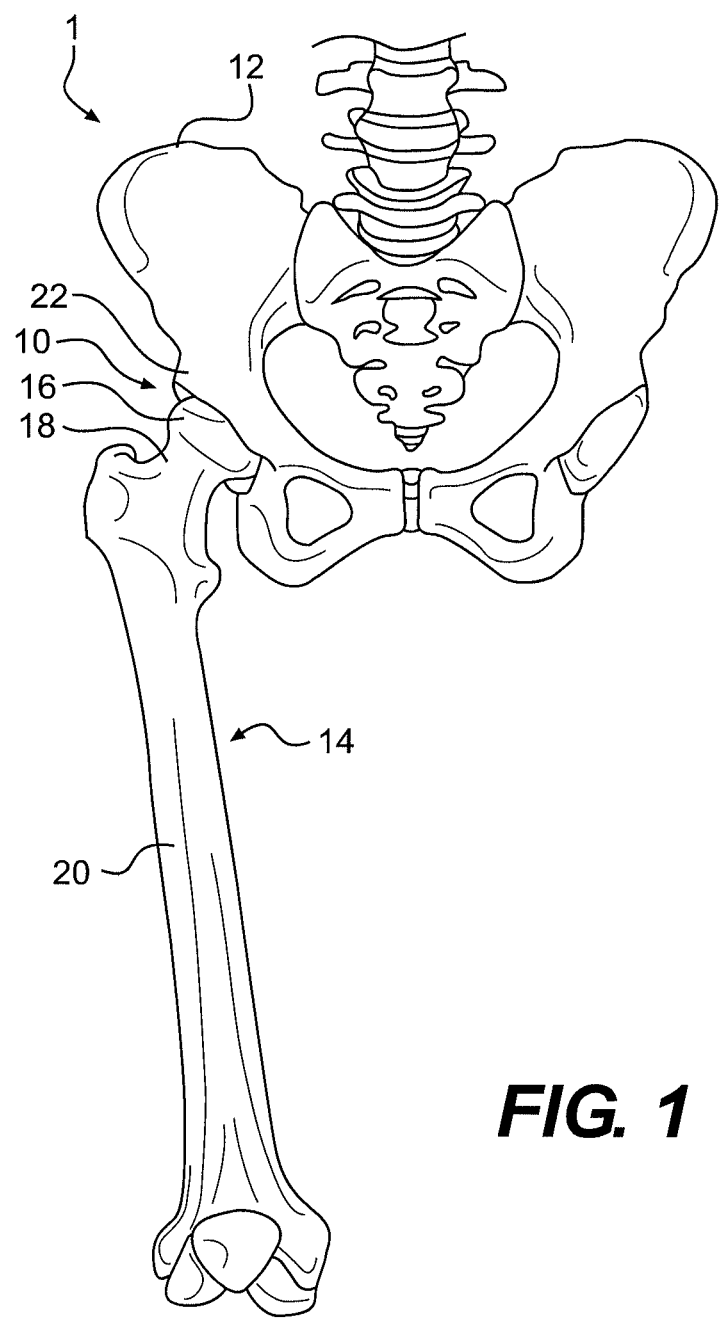
FIG. 1 provides a front view of a portion of an exemplary hip joint, the type of which may be involved in a joint replacement procedure consistent with certain disclosed embodiments.

FIG. 1 illustrates a front view of an exemplary portion of the pelvic region 1 of the human body, which includes a hip joint 10. Proper articulation of hip joint 10 contributes to many basic structural and motor functions of the human body, such as standing and walking. As illustrated in FIG. 1, hip joint 10 comprises the interface between pelvis 12 and the proximal end of femur 14. The proximal end of femur 14 includes a femoral head 16 disposed on a femoral neck 18. Femoral neck 18 connects femoral head 16 to a femoral shaft 20. Femoral head 16 fits into a concave socket in pelvis 12 called the acetabulum 22. Acetabulum 22 and femoral head 16 are both covered by articular cartilage (not shown) that absorbs shock and promotes articulation of hip joint 10.

Over time, hip joint 10 may degenerate (due, for example, to osteoarthritis) resulting in pain and diminished functionality of the joint. As a result, a hip replacement procedure, such as total hip arthroplasty or hip resurfacing, may be necessary. During a hip replacement procedure, a surgeon may replace portions of hip joint 10 with artificial prosthetic components. For example, in one type of hip replacement procedure—called total hip arthroplasty—the surgeon may remove femoral head 16 and neck 18 from femur 14 and replace them with a femoral prosthesis. Similarly, the surgeon may resect or resurface portions of acetabulum 22 using a surgical reamer or reciprocating saw, and replace the removed portions of acetabulum 22 with a prosthetic acetabular cup. Prosthetic components associated with the hip joint 10 are illustrated in FIG. 2A.

Figure 2A:
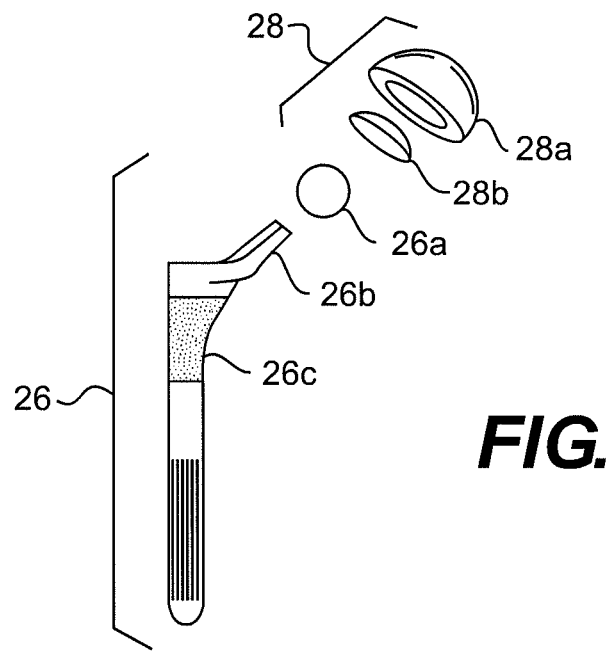
FIG. 2A provides a schematic view of exemplary components associated with a prosthetic hip joint, which may be used in a joint replacement procedure consistent with the disclosed embodiments.

As illustrated in FIG. 2A, the natural (or "native") femoral components removed during the arthroplasty may be replaced with a prosthetic femoral component 26 comprising a prosthetic head 26a, a prosthetic neck 26b, and a stem 26c. Stem 26c of prosthetic femoral component 26 is typically anchored in a cavity that the surgeon creates in the intramedullary canal of femur 14.

Similarly, the native acetabular components removed during the hip replacement procedure may be replaced with a prosthetic acetabular component 28 comprising a cup 28a that may include a liner 28b. To install acetabular component 28, the surgeon connects cup 28a to a distal end of an impactor tool and implants cup 28a into the reamed acetabulum 22 by repeatedly applying force to a proximal end of the impactor tool. If acetabular component 28 includes a liner 28b, the surgeon snaps liner 28b into cup 28a after implanting cup 28a.

Figure 2B:
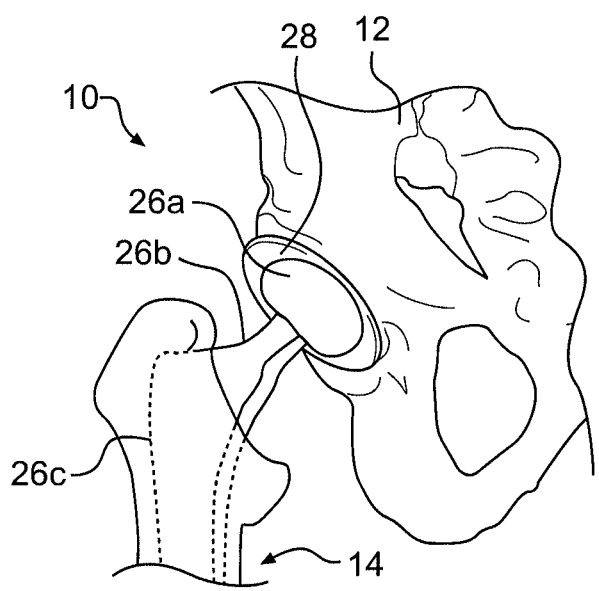
FIG. 2B illustrates a magnified view of an exemplary prosthetic hip joint in a reduced state in accordance with certain disclosed embodiments.

FIG. 2B illustrates a magnified view of an exemplary prosthetic hip joint in a reduced state. As illustrated in FIG. 2B, the stem 26c is secured within the intramedullary canal of femur 14. The prosthetic head 26a is engaged with the acetabular component 28 of pelvis 12 to form the new prosthetic joint. Before completing the surgery, the surgeon may compare certain functional parameters of the reduced prosthetic joint with a pre-operative plan to determine whether the prosthetic joint is positioned properly. Methods and systems consistent with the disclosed embodiments provide a solution for determining changes in joint parameters caused by modification of a joint resulting from orthopedic surgical procedures. Such methods and systems will be described in greater detail below.

Figure 3:
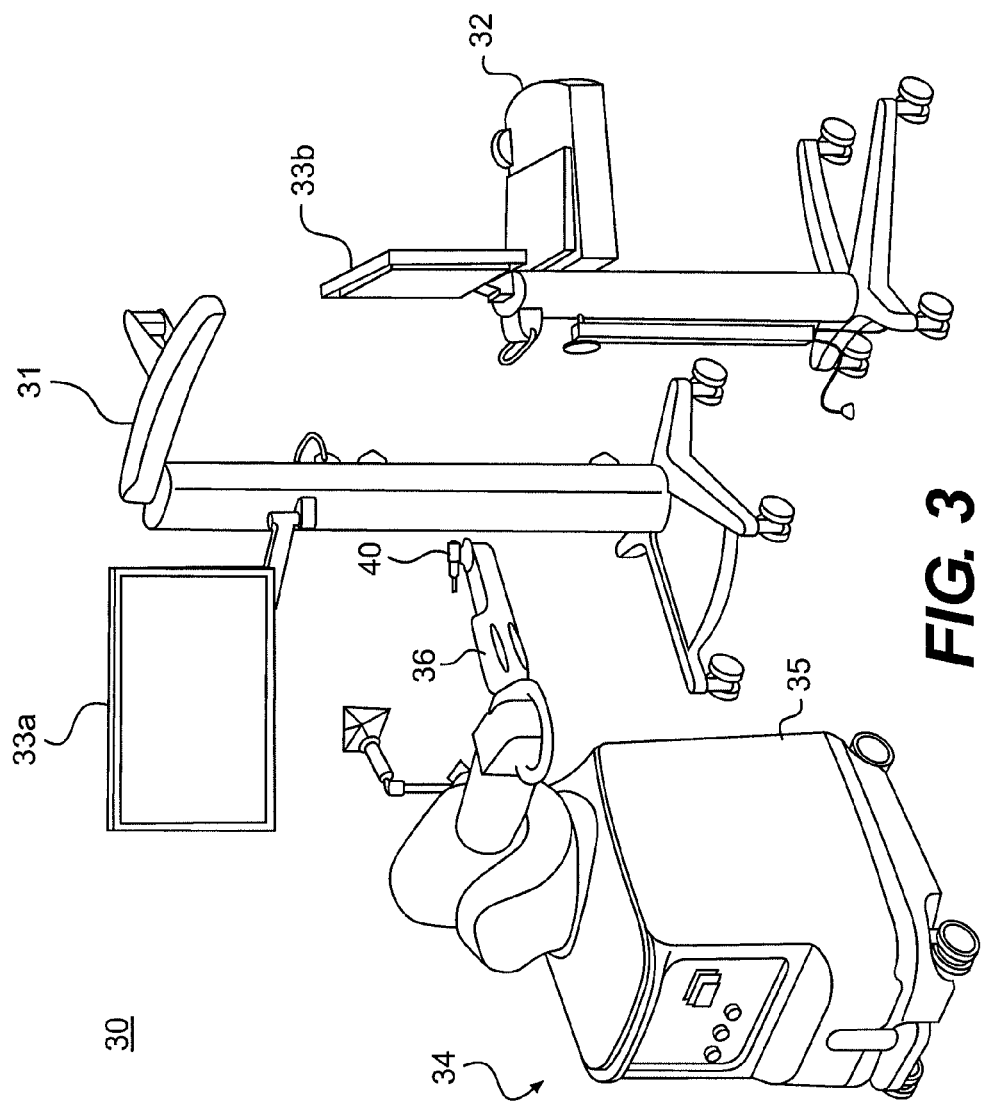
FIG. 3 provides a schematic illustration of an exemplary computer-assisted surgery (CAS) system, in which certain methods consistent with the disclosed embodiments may be implemented.

FIG. 3 provides a schematic diagram of an exemplary computer-assisted surgery (CAS) system 30, in which processes and features associated with certain disclosed embodiments may be implemented. CAS system 30 can be configured in accordance with the disclosed embodiments to perform a wide variety of orthopedic surgical procedures such as, for example, partial or total joint replacement surgeries. As illustrated in FIG. 3, CAS system 30 may comprise a tracking system 31, computer-assisted navigation system 32, one or more display devices 33a, 33b, and a robotic arm 34. It should be appreciated that CAS system 30, as well as the methods and processes described herein, may be applicable to many different types of joint replacement procedures. Although certain disclosed embodiments may be described with respect to total hip replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic arm 34 can be used in an interactive manner by a surgeon to perform a surgical procedure, such as a hip replacement procedure, on a patient. As shown in FIG. 3, robotic arm 34 includes a base 35, an articulated arm 36, a force system (not shown), and a controller (not shown). A surgical tool 40 (e.g., an end effector having an operating member, such as a saw, reamer, or burr) is coupled to the articulated arm 36, The surgeon may manipulate the surgical tool by grasping and manually moving the articulated arm 34 and/or the surgical tool 40.

The force system and controller are configured to provide control or guidance to the surgeon during manipulation of the surgical tool. The force system is configured to provide at least some force to the surgical tool via the articulated arm 36, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 30 is the RIO® Robotic Arm Interactive Orthopedic System manufactured by MAKO Surgical Corp. of Fort Lauderdale, Fla. The force system and controller may be housed within the robotic arm 34.

Tracking system 31 may include any suitable device or system configured to track the relative locations, positions, orientations, and/or poses of the surgical tool 40 (coupled to robotic arm 34) and/or positions of registered portions of a patient's anatomy, such as bones. Such devices may employ optical, mechanical, or electromagnetic pose tracking technologies. According to one embodiment, tracking system 31 may comprise a vision-based pose tracking technology, wherein an optical detector, such as a camera or infrared sensor, is configured to determine the position of one or more optical transponders (not shown). Based on the position of the optical transponders, tracking system 31 may capture the pose (i.e., the position and orientation) information of a portion of the patient's anatomy that is registered to that transponder or set of transponders.

Navigation system 32 may be communicatively coupled to tracking system 31 and may be configured to receive tracking data from tracking system 31. Based on the received tracking data, navigation system 32 may determine the position and orientation associated with one or more registered features of the surgical environment, such as surgical tool 40 or portions of the patient's anatomy. Navigation system 32 may also include surgical planning and surgical assistance software that may be used by a surgeon or surgical support staff during the surgical procedure. For example, during a joint replacement procedure navigation system 32 may display images related to the surgical procedure on one or both of the display devices 33a, 33b.

Figure 4:
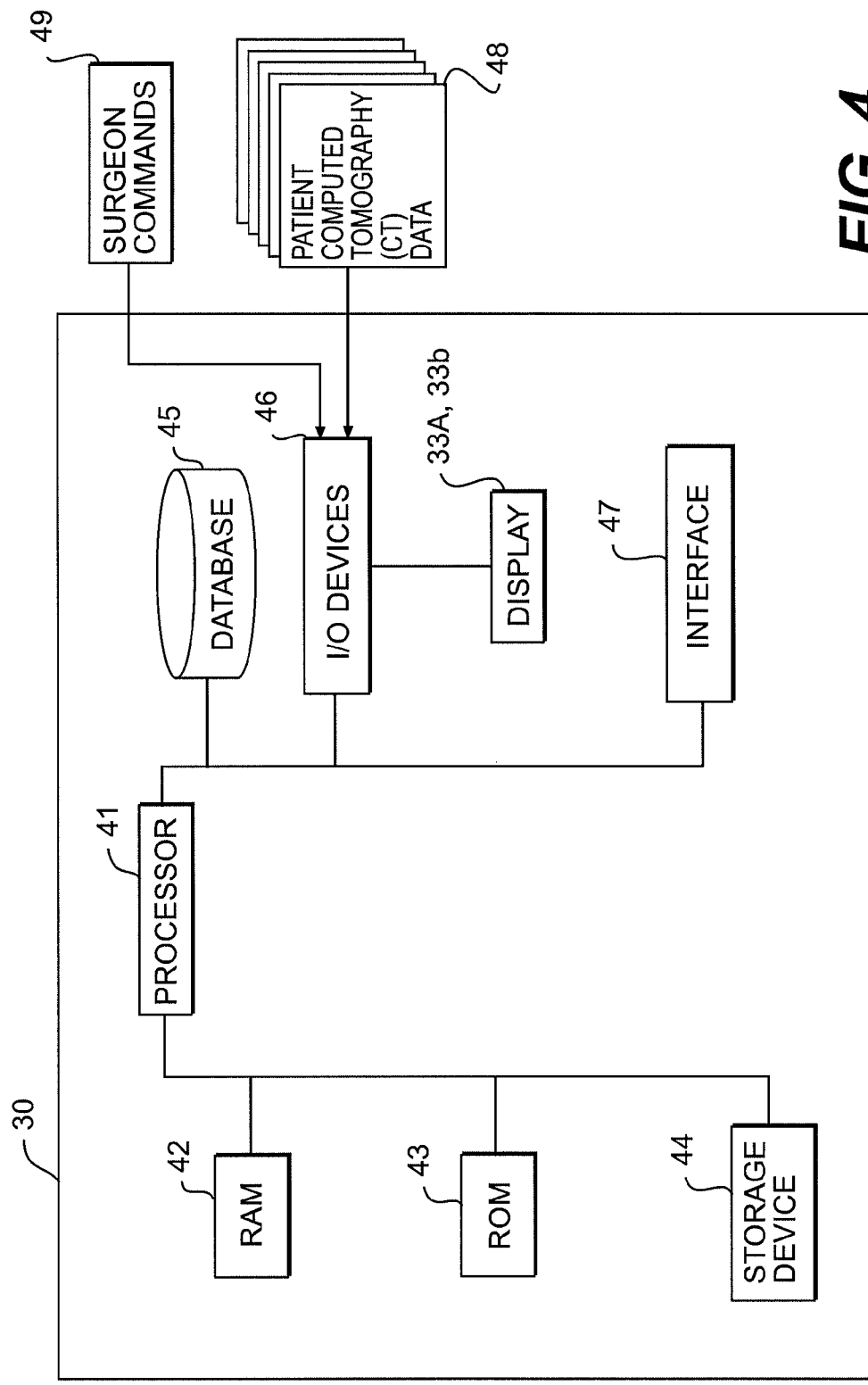
FIG. 4 provides a schematic diagram of an exemplary computer system, which may be used in one or more components associated with the CAS system illustrated in FIG. 3.

Navigation system 32 (and/or one or more constituent components of CAS system 30) may include or embody a processor-based system (such as a general or special-purpose computer) in which processes and methods consistent with the disclosed embodiments may be implemented. For example, as illustrated in FIG. 4, CAS system 30 may include one or more hardware and/or software components configured to execute software programs, such as, tracking software, surgical navigation software, 3-D bone modeling or imaging software, and/or software for determining a change in a parameter associated with a joint caused by a modification of a portion of the joint. For example, CAS system 30 may include one or more hardware components such as, for example, a central processing unit (CPU) (processor 41); computer-readable media, such as a random access memory (RAM) module 42, a read-only memory (ROM) module 43, and a storage device 44; a database 45; one or more input/output (I/O) devices 46; and a network interface 47. The computer system associated with CAS system 30 may include additional, fewer, and/or different components than those listed above. It is understood that the components listed above are exemplary only and not intended to be limiting.

Processor 41 may include one or more microprocessors, each configured to execute instructions and process data to perform one or more functions associated with CAS system 30. As illustrated in FIG. 4, processor 41 may be communicatively coupled to RAM 42, ROM 43, storage device 44, database 45, I/O devices 46, and network interface 47. Processor 41 may be configured to execute sequences of computer program instructions to perform various processes, which will be described in detail below. The computer program instructions may be loaded into RAM for execution by processor 41.

Computer-readable media, such as RAM 42, ROM 43, and storage device 44, may be configured to store computer-readable instructions that, when executed by processor 41, may cause CAS system 30 or one or more constituent components, such as navigation system 32, to perform functions or tasks associated with CAS system 30. For example, computer readable media may include instructions for causing the CAS system 30 to perform one or more methods for determining changes in parameters of a hip joint after a hip arthroplasty procedure. Computer-readable media may also contain instructions that cause tracking system 31 to capture positions of a plurality of anatomical landmarks associated with certain registered object, such as surgical tool 40 or portions of a patient's anatomy, and cause navigation system 32 to generate virtual representations of the registered objects for display on I/O devices 46. Exemplary methods for which computer-readable media may contain instructions will be described in greater detail below. It is contemplated that each portion of a method described herein may have corresponding instructions stored in computer-readable media for causing one or more components of CAS system 30 to perform the method described.

I/O devices 46 may include one or more components configured to communicate information with a user associated with CAS system 46. For example, I/O devices 46 may include a console with an integrated keyboard and mouse to allow a user (e.g., a surgeon) to input parameters (e.g., surgeon commands 49) associated with CAS system 46. I/O devices 46 may also include a display, such as monitors 33a, 33b, including a graphical user interface (GUI) for outputting information on a monitor. I/O devices 46 may also include peripheral devices such as, for example, a printer for printing information associated with CAS system 46, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 46 may include an electronic interface that allows a user to input patient computed tomography (CT) data 48 into CAS system 30. This CT data may then be used to generate and manipulate virtual representations of portions of the patient's anatomy (e.g., bones) in software.

Processes and methods consistent with the disclosed embodiments provide a solution for determining changes in parameters, such as leg length, medial/lateral offset, and/or anterior/posterior position of a joint, after a joint arthroplasty procedure. Such changes may be determined, for example, by approximating a pre-operative center of rotation of the joint and, after the procedure, estimating where the pre-operative center of the joint would be relative to pelvis 12, based on changes made to the joint. Changes in parameters of the joint may then be determined by estimating the difference between the pre-operative center of the joint and the estimated position of the pre-operative center after the procedure.

Figure 5:
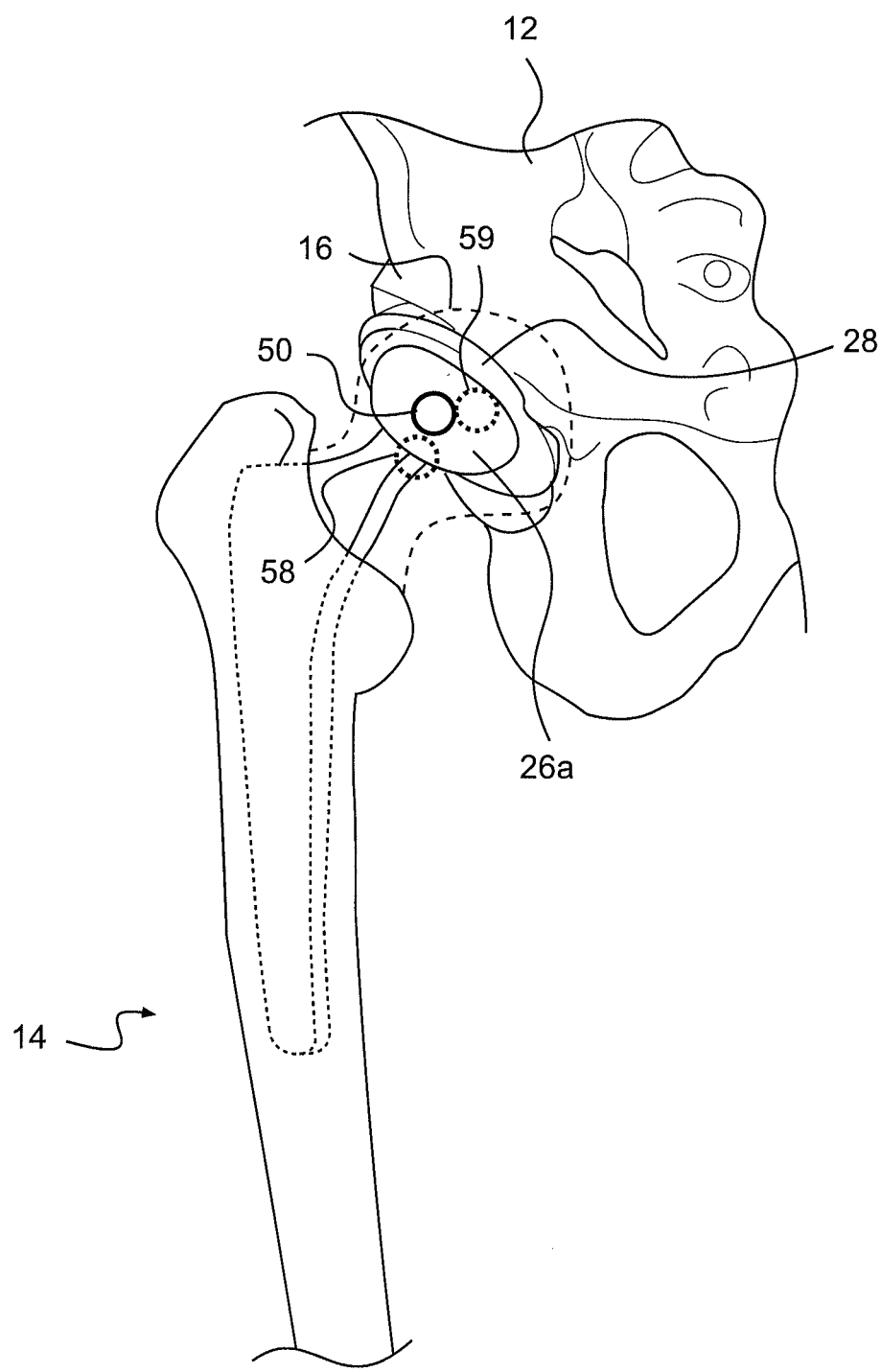
FIG. 5 provides an illustration of exemplary positions of pre- and post-operative points of reference, which may be used in methods consistent with the disclosed embodiments.

FIG. 5 provides an illustration of an exemplary prosthetic hip joint, showing a plurality of points of interest relevant to the disclosed embodiments. The prosthetic joint shown in FIG. 5 has a new center of rotation 50, which may be different than a center of rotation of the native joint 58 (as estimated prior to the surgery). That is, due to changes in the hip caused by the modification of the joint, the center of rotation of the prosthetic joint 50 may differ from the center of rotation of the native joint 58.

The presently disclosed methods approximate joint parameters such as leg length and offset by tracking or predicting the position of the pre-operative center of rotation relative to the femur, and projecting this position into post-operative pelvic space. FIG. 5 illustrates the tracked position of the pre-operative center of rotation in pelvic space as numeral 59, which is shown in relation to a virtual representation of the native femoral head 16. Changes in joint parameters, such as leg length and offset, may then be determined by estimating the difference between the pre-operative center of rotation 58 of the native joint in pelvic space and the position 59 of the pre-operative center of rotation in pelvic space, when the pre-operative center of rotation 58 is maintained in a constant position relative to the reconstructed femur. According to an exemplary embodiment, the processes and methods for determining changes in joint parameters consistent with the disclosed embodiments may be implemented, at least in part, by CAS system 30. FIGS. 6-9 illustrate exemplary embodiments associated with methods for calculating joint modification parameters.

Figure 6:
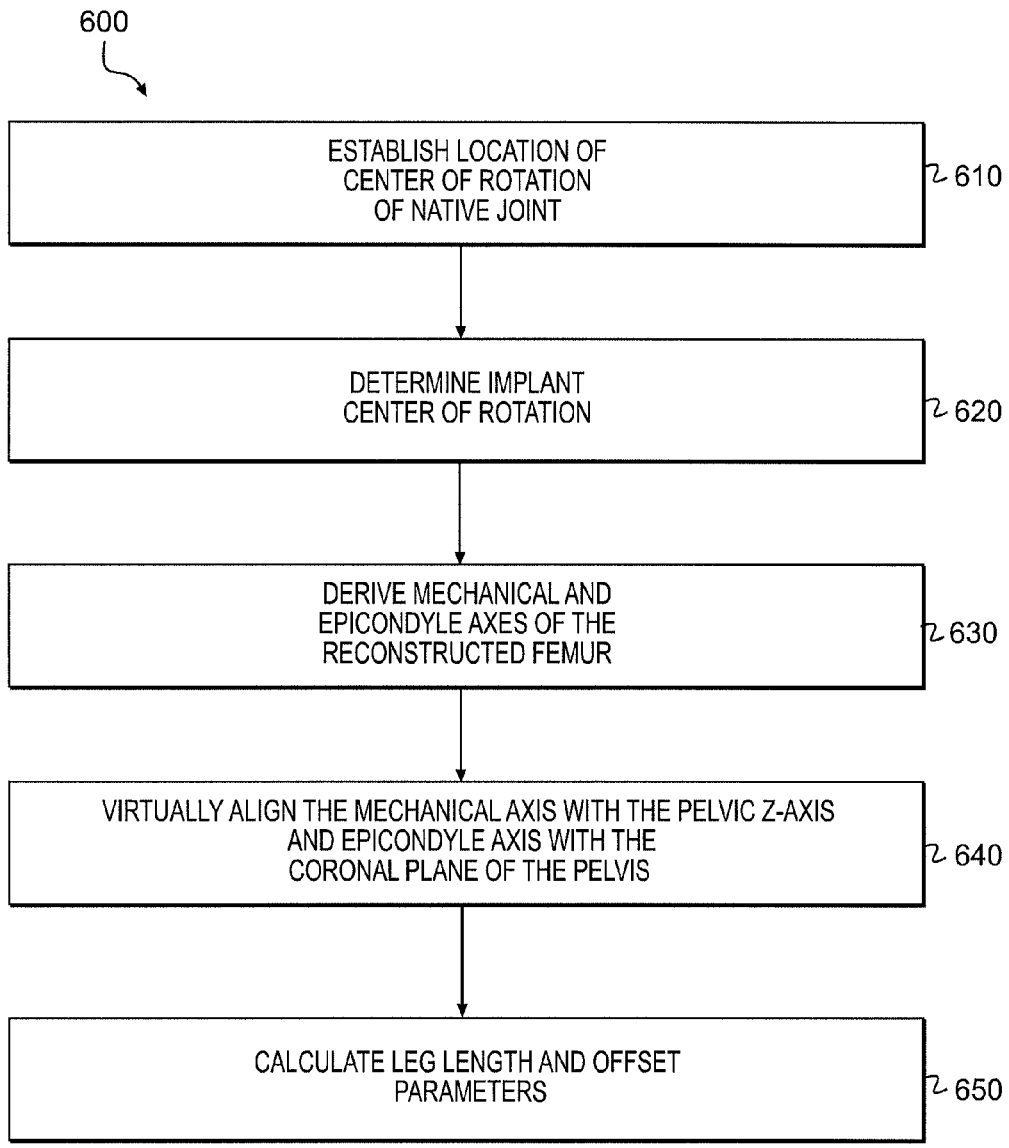
FIG. 6 provides a flowchart depicting an exemplary method for determining changes in parameters of a hip joint, in accordance with certain disclosed embodiments.

FIG. 6 provides a flowchart 600 illustrating an exemplary method for determining joint parameters. As illustrated in FIG. 6, the process comprises establishing a position of the center of the rotation of the native joint that is to be surgically repaired (Step 610). The position of the center of the native joint may be established using one of a number of different techniques. For example, the position of the center of rotation of the native joint may be estimated, by either a user or CAS system 30, as the geometric center of the native femoral head 16, a portion of which is substantially spherical in shape. Alternatively or additionally, the position of the center of rotation may be estimated as the geometric center of the portion of the sphere formed by the concave profile of acetabulum 22.

According to one embodiment, the position of the center of the native femoral head 16 or acetabulum 22 may be estimated by analyzing computed tomography (CT) data associated with the patient's joint. For example, prior to a joint replacement procedure, CT scans of the subject joint (and surrounding area) of the patient may be taken. The patient's CT data may be used to generate a virtual representation of the subject joint (e.g., hip) and the associated bones. This virtual representation of the hip joint may include, for example, a three dimensional (3-D) software model of femur 14 and pelvis of the hip joint. Interactive software associated with CAS system 30 may analyze (or allow a user to analyze) the 3-D software model of femoral head 16 (and/or acetabulum 22) to derive the center of femoral head 16 (and/or acetabulum 22). According to one embodiment, the interactive software may be configured to allow the user to select a plurality of points about the surface of the virtual representation of the femoral head 16. A software algorithm may then analyze the plurality of points and estimate the geometric center associated with the selected points.

According to yet another embodiment, the center of rotation of the native joint may be estimated using a kinematic tracking algorithm. This technique involves tracking the position of sensors or markers that are attached to femur 14. The relative position of sensors or markers may be continuously monitored by tracking system 31 and navigation system 32 as femur 14 is rotated through a plurality of orientations about the joint. As the positions of the markers are captured, a hip kinematic algorithm estimates a geometry (typically spherical) formed by accumulation of the tracked position data and determines a center associated with the estimate geometry. The center of the geometry may be established as the center point of rotation of the native joint.

Once the center of rotation 58 of the native joint is determined, a processor associated with CAS system 30 may establish the position of the center of rotation in both a femoral space and a pelvic space. That is, CAS system 30 may define the position of the center of rotation relative to a virtual representation of femur 14 so that a change in the position of the virtual representation of femur 14 relative to pelvis 12 results in a corresponding change in position of the center of the native femoral head relative to pelvis 12. Similarly, CAS system 30 may also define the position of the center of rotation relative to a virtual representation of pelvis 12. CAS system 30 may store each of these relative positions in memory for later retrieval. In storing the positions of the center of rotation of the joint in both femoral and pelvic space, CAS system 30 is able to track the position of the pre-operative center of rotation as the joint changes during the surgery. Thus, even after the center of rotation of the joint is changed during a total hip arthroplasty, CAS system 30 maintains the ability to track the center of rotation of the joint relative to both femur 14 and pelvis.

After the center of rotation of the native joint has been estimated, the surgeon may perform a surgical procedure that results in a modification of the joint. Such a procedure may involve dislocation of the joint, removal of some or all of the native components (e.g., femoral head 16 or acetabulum 22) of the joint, replacement of the removed portions of the native components with prosthetic components, and reduction of the joint. Upon completion of the joint modification procedure, a center of rotation of the implanted joint may be determined (Step 620).

According to one embodiment, the center of rotation of the native joint may be derived using a kinematic tracking algorithm described above. That is, tracking system 31 and navigation system 32 may track the position of the native femur 14 (using electronic markers affixed to femur 14) as it is rotated through a plurality of positions about the native joint. As the movements of femur 14 are captured, software associated with navigation system 32 uses a hip kinematic algorithm to estimate a geometry (typically substantially spherical) derived from the accumulation of the tracked position data. The kinematic software may identify the center of the estimated geometry. The center of the geometry may be established as the center point of rotation of the native joint.

Figure 7:
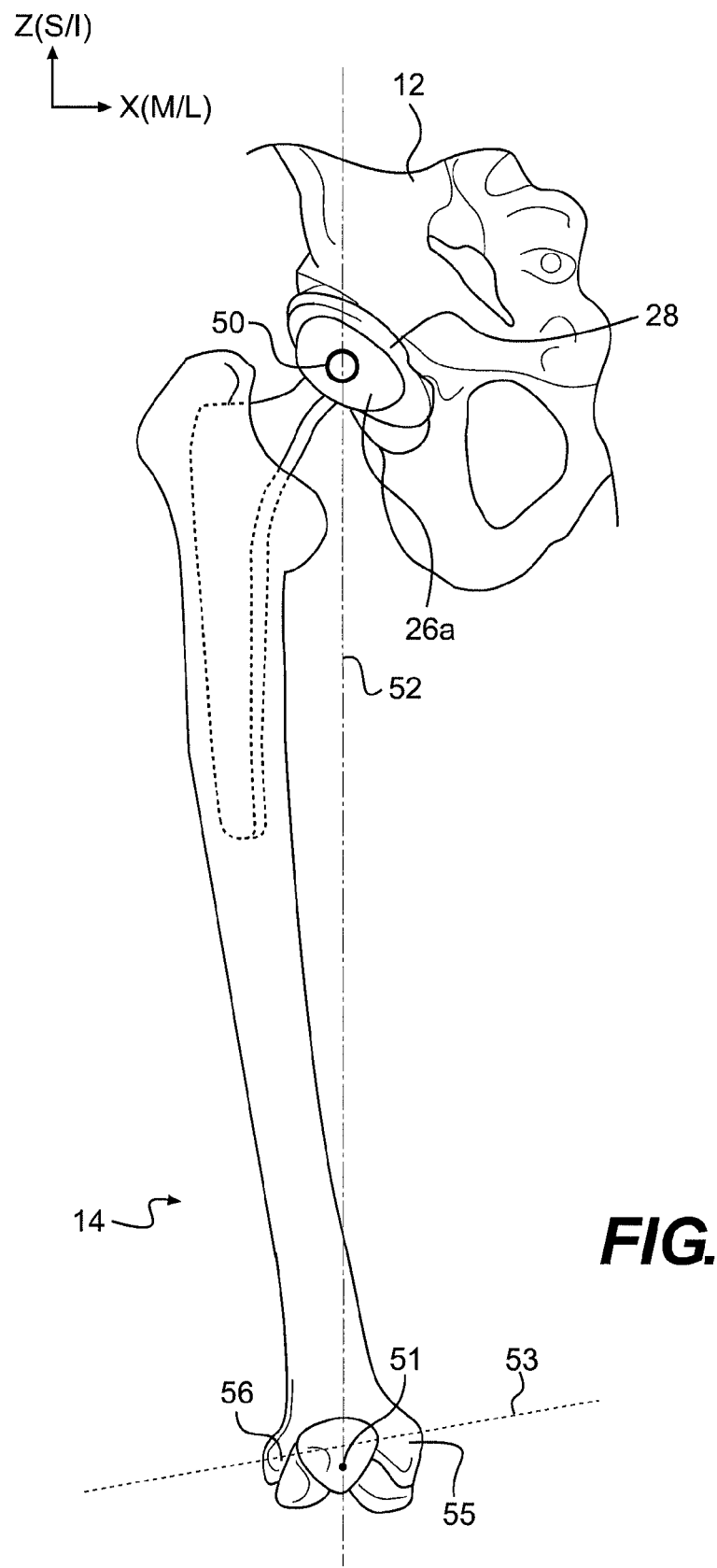
FIG. 7 provides a front view of an exemplary prosthetic hip joint in a reduced state, consistent with the disclosed embodiments.

After determination of the center of rotation of the implanted joint, the mechanical and epicondyle axes associated with the reconstructed joint may be established (Step 630). For example, as illustrated in FIG. 7, a mechanical axis 52 associated with the reconstructed femur 14 may be established in CAS system software as a virtual line passing through the center of rotation 50 of the implanted joint and a midpoint 51 located between the medial epicondyle 55 and the lateral epicondyle 56 of femur 14. CAS system 30 may also establish an epicondyle axis 53 as a virtual line passing through the transverse of the medial and lateral epicondyles 55, 56.

Upon establishing the mechanical and epicondyle axes of the reconstructed femur 14, the virtual model of the femur is orientated such that the mechanical axis is parallel to the superior/inferior ("S/I") axis of pelvis 12 (Step 640). Also in step 640, the virtual model of the femur is oriented such that the epicondyle axis is parallel to the coronal plane (z-x plane) of pelvis 12. According to one embodiment, software associated with CAS system 30 may position mechanical axis 51 of a virtual model of the femur as parallel with the S/I axis (or z-axis of FIG. 7). Similarly, software associated with CAS system 30 may position epicondyle axis 53 of the virtual model of the femur as parallel with the coronal plane (i.e., z-x plane of FIG. 7). Positioning the virtual model of the reconstructed femur 14 in such a way ensures that the virtual representation of the leg is positioned in a meaningful and repeatable manner. Furthermore, performing the positioning step using CAS software (rather than manually by a surgeon) may significantly increase reliability, repeatability, and accuracy of the subsequent calculations of joint parameters.

Once the reconstructed femur 14 has been virtually positioned, joint parameters, such as leg length, offset, and/or anterior/posterior position may be calculated (Step 650). To calculate joint parameters in accordance with an exemplary embodiment, CAS system 30 may first determine the tracked position 59 of the pre-operative center of rotation in pelvic space. Because the position of the center of rotation of the native joint was originally mapped to the virtual representation of femur 14, the tracked position 59 of the center of rotation of the native joint can be derived based on the position of the reconstructed femur 14. This position may then be projected into the pelvic space.

Once the tracked position 59 of the center of rotation has been determined with respect to the reconstructed femur 14, CAS system 30 may retrieve data indicative of the original center of rotation 58 of the native joint that was stored relative to the pelvic coordinate system (also referred to herein as the pelvic space). The difference between the position 58 of the original center of rotation of the native joint in pelvic space and the tracked position 59 of the center of rotation of the native joint (relative to the reconstructed femur 14) represents the change in the parameters of the joint. In particular, leg length may be calculated by determining the difference between the original position 58 and the tracked position 59 in the S/I axis (z-axis relative to pelvis 12). The medial/lateral offset may be calculated by determining the difference between the original position 58 and the tracked position 59 in the M/L axis (x-axis relative to pelvis 12).

The method described in connection with flowchart 600 of FIG. 6 provides one exemplary embodiment for calculating changes in parameters due to a joint modification surgery. It is contemplated that additional, different, and/or fewer steps may be associated with the method shown in FIG. 6 without departing from the scope of the present disclosure. For example, although FIG. 6 describes that the virtual positioning of the reconstructed femur 14 is based on the mechanical axis 52 and epicondyle axis 53, it is contemplated that different axes or reference points may be used to ensure that the reconstructed femur 14 is placed in the predetermined pose. Accordingly, FIG. 8 has been provided to illustrate another exemplary embodiment for determining changes in joint parameters.

Figure 8:
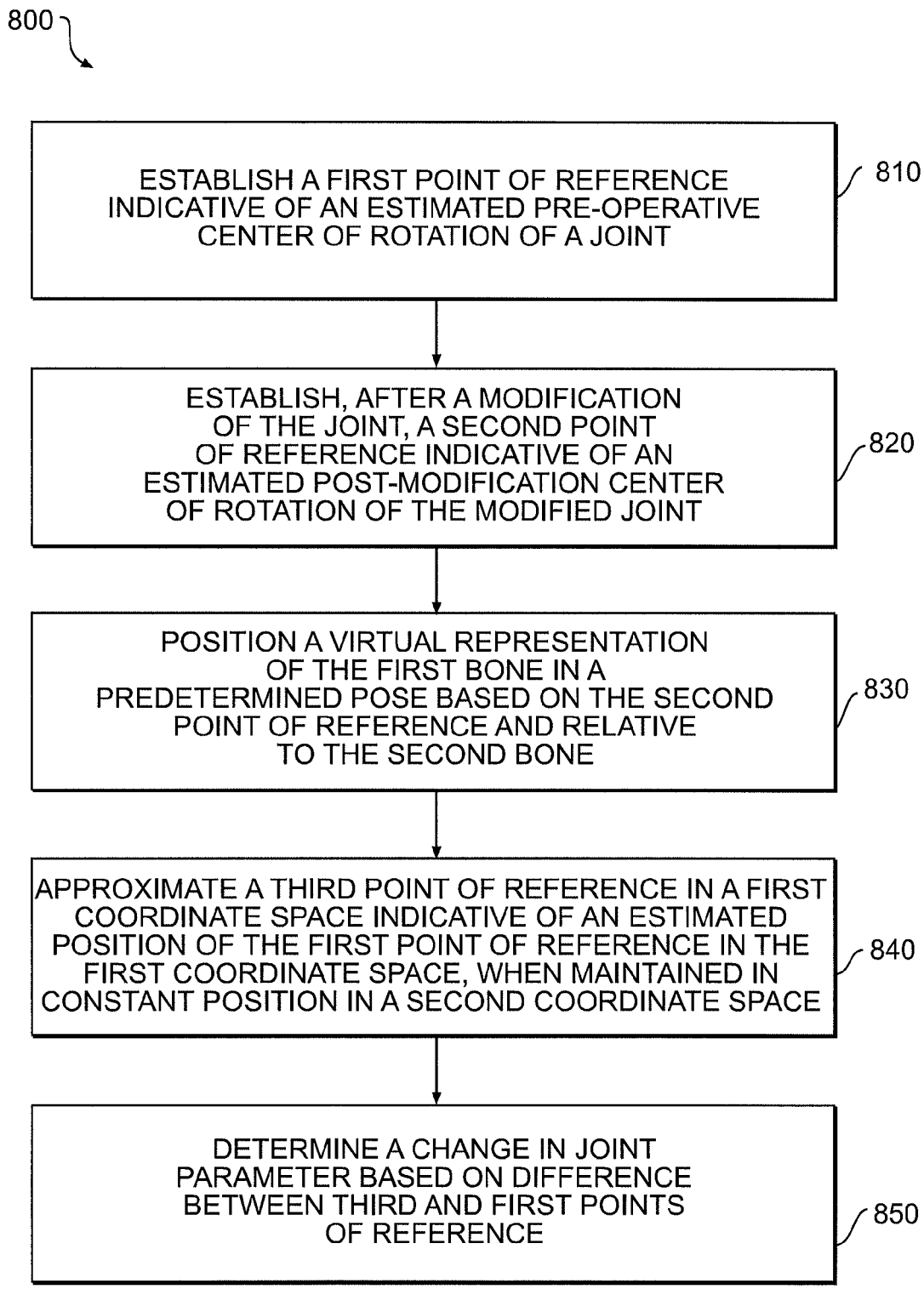
FIG. 8 provides a flowchart showing an exemplary method for determining a change in a parameter associated with a joint, in accordance with certain disclosed embodiments.

FIG. 8 provides flowchart 800 illustrating a process for determining a change in a parameter associated with a joint caused by a modification of a portion of the joint. The process may commence with the establishment of a first point of reference 58 indicative of an estimated pre-operative center of rotation of a joint to be modified by a joint replacement procedure (Step 810). As described above in connection with flowchart 600 of FIG. 6, the pre-operative center of rotation may be established using a number of different techniques. One technique involves estimating the pre-operative center of rotation of the joint based on a virtual representation of the joint created from patient CT data. For example, for embodiments involving hip joint replacements, a first point of reference may be established as the estimated center of native femoral head 16 or the estimated center of native acetabulum 22. CAS system 30 may record the first point of reference in both a femoral space (i.e., in a virtual coordinate space corresponding to the software representation of the native femur 14) and a pelvic space (i.e., in a virtual coordinate space corresponding to the software representation of the native pelvis).

After the first point of reference 58 has been established and stored, the surgeon may perform a surgical procedure that results in a modification of the joint. Such a procedure may involve, for example, replacement of the native femoral head 16 and acetabulum 22 with a prosthetic femoral component 26 and acetabular cup 28. After the procedure, a second point of reference 50 that is indicative of an estimated post-modification center of rotation of the modified joint may be determined (Step 820). As explained above, the post-modification center of rotation of the modified joint may be estimated by CAS software that uses a hip kinematic algorithm to derive the center of rotation based on the tracked positions of the leg as the surgeon moves the reconstructed femur 14 about the replacement joint.

Upon estimating the second point of reference associated with the modified joint, a virtual representation of the first bone may be positioned in a predetermined pose based on the second point of reference and relative to the second bone (Step 830). For example, a software model associated with femur 14 may be virtually positioned and rotated relative to the center point of rotation of the reconstructed joint in a specific predetermined pose. According to an exemplary embodiment described above with respect to Step 640, this positioning may involve establishing a mechanical axis 52 and an epicondyle axis 53 of the reconstructed femur 14 in virtual (i.e., software) space. The mechanical axis 52 of the virtual representation of the reconstructed femur 14 may be virtually positioned as parallel with the superior/inferior ("S/I") axis of pelvis 12. The epicondyle axis 53 of the virtual representation of the reconstructed femur 14 may be virtually positioned as parallel with the coronal (z-x) plane of pelvis 12.

After the virtual positioning of the first bone in the predetermined pose, a third point of reference 59 may be established relative to the reconstructed pelvis (Step 840). The third point of reference 59 may be indicative of an estimated position of the first point of reference relative to pelvis 12 based on the virtual positioning of the first bone. As explained above with respect to FIG. 5, this position (shown in FIG. 5 as element 59) may correspond to a tracked position of the first point of reference relative to the reconstructed femur 14, as projected into the pelvic space.

Software associated with CAS system 30 may be configured to estimate a change in one or more joint parameters based on a difference in the positions of the third point of reference 59 and first point of reference 58 (Step 850). According to one embodiment, leg length may be calculated by determining the difference between the position of the first point of reference 58 and the position of the third point of reference 59 in the S/I axis relative to pelvis 12. The medial/lateral offset may be calculated by determining the difference between the first point of reference 58 and the position of the third point of reference 59 in the M/L axis relative to pelvis 12. The difference in anterior/posterior position may be calculated by determining the difference between the first point of reference 58 and the position of the third point of reference 59 in the anterior/posterior axis relative to pelvis 12.

Figure 9:
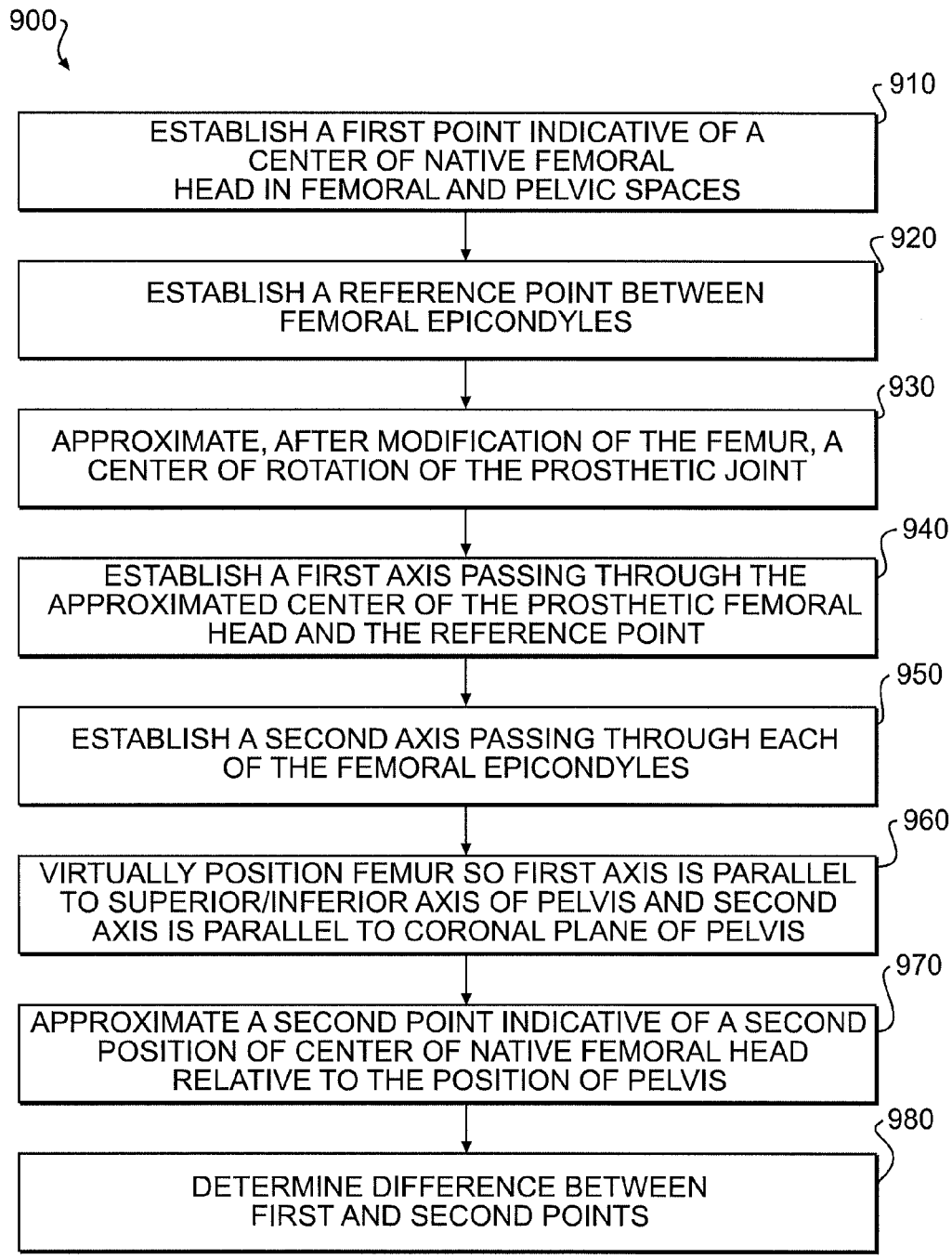
FIG. 9 provides a flowchart depicting another exemplary method for determining a change in a parameter of a hip joint, consistent with certain disclosed embodiments.

FIG. 9 provides flowchart 900 illustrating yet another exemplary embodiment of a computer-implemented process for determining a change in a parameter associated with a joint, particularly as it relates to total hip arthroplasty. The process may commence with the approximation of a first point indicative of a center of a native femoral head in femoral space (Step 910). For example, prior to a joint replacement procedure, a virtual representation of the hip joint, femur 14, and pelvis may be generated based on patient CT data. Interactive software may be configured to allow the user to select a plurality of points about the surface of the virtual representation of the native femoral head 16. A software algorithm may then analyze the plurality of points and estimate a geometric center associated with the selected points. CAS software 30 may store information indicative of the position of the center of the native femoral head relative to femur 14 and pelvis, for later retrieval and analysis.

At step 920, CAS system 30 may establish a reference point between the femoral epicondyles 55, 56. According to one embodiment, CAS system 30 may determine, based on an analysis of the geometry of the virtual representation of femur 14, a midpoint 51 between the medial epicondyle 55 and the lateral epicondyle 56 at the distal end of femur 14. CAS system 30 may then establish midpoint 51 as the reference point, which may be used for subsequent virtual alignment of the reconstructed femur 14. It is contemplated that CAS system 30 may establish additional and/or different reference points than midpoint 51 of the femoral epicondyles 55, 56. For example, CAS system 30 may be configured to establish the center of the patella as the reference point, which does not necessarily correspond with midpoint 51 of the femoral epicondyles 55, 56.

After the reduction of the hip joint during the hip replacement procedure, CAS system 30 may approximate a center of rotation 50 of the prosthetic joint (Step 930). According to one embodiment, CAS system 30 may derive the center of rotation of the reduced prosthetic hip joint using the hip kinematic algorithm technique described above. Alternatively or additionally, CAS system 30 may be configured to estimate the center of rotation using data captured by the surgeon's exploration of the surface of the implanted prosthetic head with a registered probe. For example, tracking system 31 and navigation system 32 may track the position of an "exploratory probe" as the surgeon touches a plurality of points on the surface of the implanted prosthetic head 26a. CAS system 30 may be configured to approximate the center of the prosthetic femoral head 26a as the estimated center of a geometry formed by the accumulation of the plurality of points.

At steps 940 and 950, CAS system 30 may establish first and second axes associated with the virtual representation of the reconstructed femur 14. The first axis may comprise a virtual line that passes through the approximated center of the prosthetic femoral head and the approximated reference point between the femoral epicondyles (as determined at step 920). According to one embodiment, the first axis comprises the mechanical axis 52 of the reconstructed femur 14. The second axis may comprise a virtual line that passes laterally through the approximated center of each of the femoral epicondyles. According to one embodiment, the second axis comprises the epicondyle axis 53 of femur 14.

Upon establishing first and second axes corresponding to the virtual representation of the reconstructed femur 14, CAS system 30 may virtually position the reconstructed femur 14 so that the first axis is parallel to the superior/inferior axis (z-axis shown in FIG. 7) of pelvis 12 and the second axis is parallel to the coronal plane (z-x plane shown in FIG. 7) of pelvis 12 (Step 960). That is, software associated with CAS system 30 may position a 3-D model corresponding to femur 14 in software space so that the axis passing through the center of rotation of the reconstructed femur 14 and the reference point established between the femoral epicondyles is parallel with the S/I axis of pelvis 12. Similarly, the software associated with CAS system 30 may position the 3-D model corresponding to femur 14 in software space so that the axis passing laterally through the femoral epicondyles is parallel with the z-x plane of pelvis 12.

After positioning the virtual representation of the reconstructed femur, CAS system 30 may approximate a second point 59 indicative of a second position of the center of the native femoral head relative to the position of pelvis 12 (Step 970). As explained, the second point 59 may be determined by tracking the point corresponding to the pre-operative position 58 of the center of rotation of the joint relative to the virtually-positioned of the reconstructed femur 14. CAS system 30 may then project the tracked position of the second point onto the pelvic space. This projected position may be established as the second (i.e., tracked) point 59 of the center of the native femoral head.

At step 980, CAS system 30 may determine the difference between the second point and the first point (as determined prior to modification of the joint). Software associated with CAS system 30 may then estimate a change in one or more joint parameters based on a difference in the positions of the third and first points. As explained, leg length may be calculated by determining the amount by which the first and second positions of the native femoral head differ in the pelvic S/I direction. The medial/lateral offset may be calculated by determining the amount by which the first and second positions of the native femoral head differ in the pelvic M/L direction. The difference in anterior/posterior position may be calculated by determining the amount by which the first and second positions of the native femoral head differ in the pelvic anterior/posterior direction.

Figure 10:
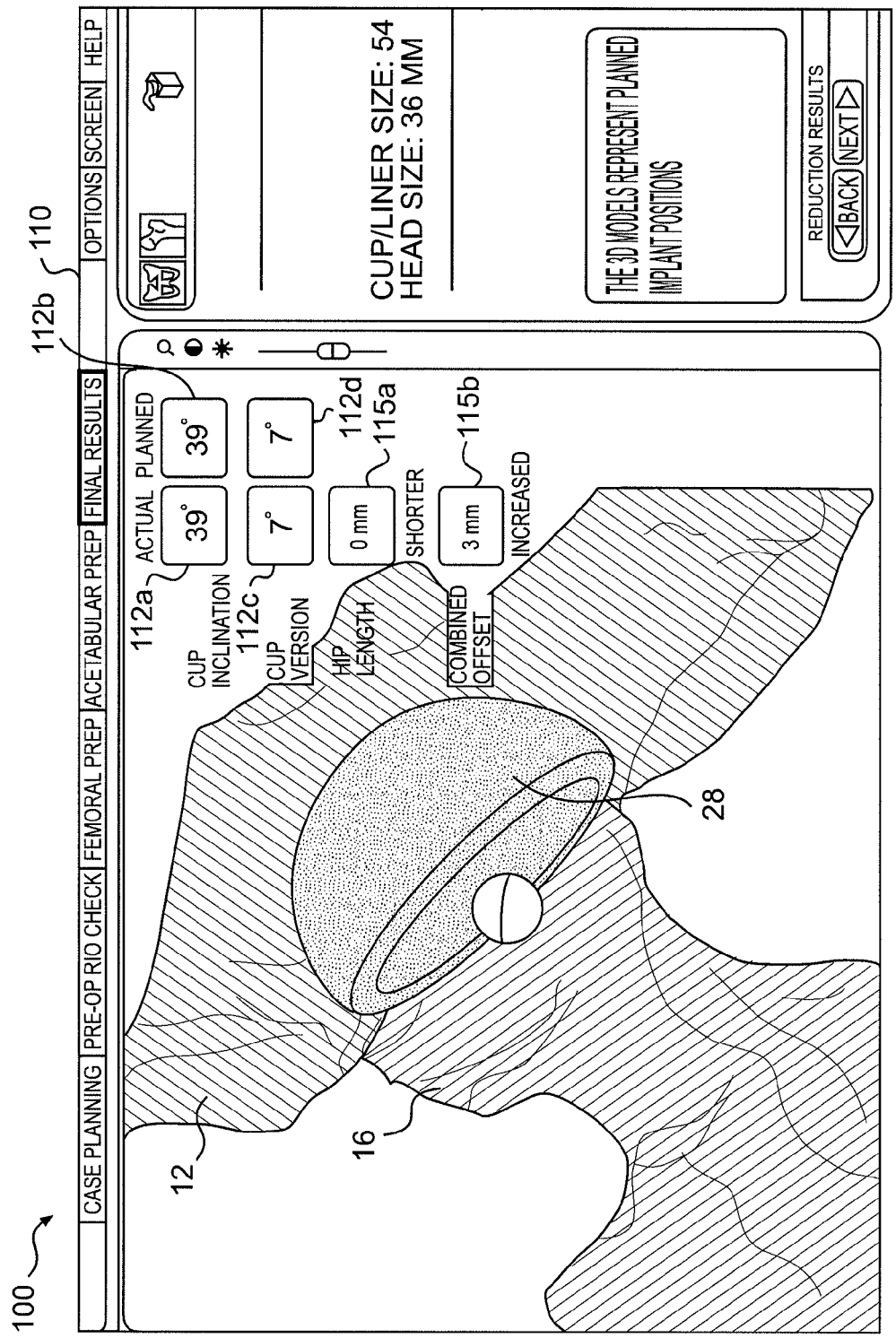
FIG. 10 illustrates an embodiment of a user interface that may be displayed during a surgical procedure in accordance with certain exemplary disclosed embodiments.

Once the difference(s) in joint parameters have been calculated, CAS system 30 may display one or more of the parameters on a graphical user interface of one or more displays 33a, 33b. Alternatively or additionally, CAS system 30 may also display a virtual representation of one or more of the pre-operative position 58 of the center of rotation of the joint, the post-operative position 50 of the center of rotation of the modified joint, and/or the tracked position 59 of the pre-operative center of rotation of the joint relative to the position of the reconstructed joint. Based on the displayed information, the surgeon may determine whether adjustment to the prosthetic joint is required prior to finishing the surgery. FIG. 10 provides an exemplary screen shot 100 of a graphical user interface 110 that may be provided to a user via display(s) 33a, 33b.

As illustrated in FIG. 10, graphical user interface 110 may include fields that display, among other things, parameters associated with the implanted prosthetic hardware. For example, FIG. 10 comprises a graphical user interface 110 corresponding to an arthroplastic procedure involving the resurfacing of a patient's acetabulum 22 and installation of a prosthetic acetabular cup 28. As such, the graphical user interface 110 comprises a virtual representation of the modified joint and includes parameters 112a-112d indicative of an actual and planned inclination and version of a prosthetic acetabular cup 28. As such, the graphical user interface 110 may also include fields 115a, 115b that display the relative change in the parameters associated with the modified joint such as, for example, hip (or leg) length and combined (medial/lateral) offset. It should be noted that the information shown in graphical user interface 110 of FIG. 10 is exemplary only. It is contemplated that additional, fewer, and/or different parameters may be displayed depending, for example, on the type of procedure (e.g., total hip replacement, partial hip replacement, hip resurfacing, etc.) and the surgeon's preferences. For example, in addition to leg length and offset, a surgeon may also be interested in the change in anterior/posterior position resulting from the joint modification. As such, the surgeon may customize the display by enabling an option for displaying a parameter corresponding to the difference in anterior/posterior position.

The presently disclosed systems and methods provide a solution that enables a computer-assisted surgical system to determine changes in joint parameters resulting from modifications made to the joint during surgery in a fast and repeatable way. By enabling virtual positioning of the reconstructed femur 14 in software space, processes consistent with the disclosed embodiments ensure that the reference for tracking the position of the pre-operative center of rotation relative to the reconstructed joint is consistently oriented in the same, predetermined pose, regardless of the actual position of the patient's leg. As a result, error associated with measurements made based on unreliable, human alignment of the reconstructed femur 14 may be significantly reduced. Moreover, systems and methods consistent with the disclosed embodiments measure changes in joint parameters based on a comparison between a first position of a reference point determined pre-operatively and a second position of the reference point determined (or tracked) in post-operative space.

It will be apparent to those skilled in the art that various modifications and variations can be made to the disclosed systems and associated methods for determining a change in a parameter associated with a joint caused by a modification of a portion of the joint. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A computer-assisted surgery system comprising:
   a display;
   an input device configured to receive data input by a user;
   a processor, operatively coupled to the input device and the display and configured to:
      establish a first position of a pre-operative center of rotation of a joint in a first coordinate space of a first bone and a second coordinate space of a second bone;
      establish a second position of the pre-operative center of rotation of the joint in the first coordinate space of the first bone, wherein the second position is a projection into the first coordinate space of the first bone of the position of the pre-operative center of rotation maintained in a constant position in the second coordinate space of the second bone; and determine a change in a parameter associated with the joint based on the first and second positions; and output a result indicative of the determined change in the parameter to the display.

2. The computer-assisted surgery system of claim 1, wherein the processor is configured to establish the second position of the pre-operative center of rotation of the joint by:

estimating, by the processor after modification of the joint, a position of a center of rotation of the modified joint; and positioning, by the processor in a virtual coordinate space, a virtual representation of the second bone in a predetermined pose based, at least in part, on the center of rotation of the modified joint.

3. The computer-assisted surgery system of claim 1, wherein the joint is a hip joint, and wherein the first coordinate space is a pelvic space and the second coordinate space is a femoral space.

4. The computer-assisted surgery system of claim 3, wherein the processor is configured to establish the second position of the pre-operative center of rotation of the joint by:

estimating, by the processor after modification of the hip joint, a position of a center of rotation of the modified hip joint; and positioning, by the processor in a virtual coordinate space, a virtual representation of a femur in a predetermined pose based, at least in part, on the center of rotation of the modified hip joint.

5. The computer-assisted surgery system of claim 4, wherein the processor is configured to position the virtual representation of the femur in the predetermined pose by:

establishing a first axis associated with the femur, the first axis comprising a virtual axis passing through the center of rotation of the modified hip joint and an estimated midpoint between epicondyles of the femur; and establishing a second axis associated with the femur, the second axis comprising a virtual transverse axis passing through the epicondyles of the femur, wherein the virtual representation of the femur is positioned in the virtual coordinate space so that the first axis is substantially parallel with a superior/inferior axis of the pelvis and the second axis is substantially parallel with a coronal plane of the pelvis.

6. The computer-assisted surgery system of claim 1, further comprising a data storage device containing computed tomography (CT) data associated with the joint of a patient, wherein the processor is further configured to:

retrieve the CT data associated with the joint;

receive information indicative of a geometric feature of the joint; and estimate the center of rotation of the joint based on the analysis of the geometric feature.

7. The computer-assisted surgery system of claim 6, wherein the processor is further configured to:

generate a virtual representation of at least a part of the first bone, based on the obtained CT data associated with the joint;

capture positions of a plurality of anatomical landmarks associated with the first and second bones; and electronically track a position of the virtual representation of the first bone based on the captured position.

8. The computer-assisted surgery system of claim 7, wherein the processor is configured to establish the first position of the pre-operative center of rotation of the joint by:

defining the first position relative to the virtual representation of the second bone so that a change in the position of the virtual representation of the second bone relative to the first bone results in a corresponding change in position of the pre-operative center of rotation of the joint relative to the first bone, and wherein establishing the second position of the pre-operative center of rotation of the joint comprises:

electronically tracking a position of the pre-operative center of rotation of the joint; and determining, upon positioning of the second bone in the predetermined pose in the virtual coordinate space, the second position as the electronically-tracked position of the pre-operative center of rotation of the joint.

9. A computer-assisted surgery system for determining a change in a parameter associated with a joint caused by a modification of a portion of the joint, the method comprising:

a display;

an input device; and a processor, operatively coupled to the input device and the display and configured to:

establish a first point of reference relative to a first bone of a joint, the first point of reference indicative of an estimated pre-operative center of rotation of the joint in pelvic space;

establish, after a modification of the joint, a second point of reference indicative of an estimated post-modification center of rotation of the joint;

position a virtual representation of the first bone in a predetermined pose based on the second point of reference and relative to a second bone;

approximate, based on the positioning of the virtual representation of the first bone in the predetermined pose, a third point of reference in pelvic space indicative of a position of the first point of reference maintained in a fixed relationship relative to the first bone;

estimate a change in a parameter associated with the joint based on a difference between the third point of reference and the first point of reference; and output a result indicative of the estimated change in the parameter to the display.

10. The computer-assisted surgery system of claim 9, wherein the joint is a hip joint, the first bone is a femur of the hip joint, and the second bone is a pelvis of the hip joint.

11. The computer-assisted surgery system of claim 10, wherein the processor is configured to position the virtual representation of the first bone in a predetermined pose by:

establishing a first axis associated with the femur, the first axis comprising a virtual axis passing through the second point of reference and an estimated midpoint between epicondyles of the femur; and establishing a second axis associated with the femur, the second axis comprising a virtual transverse axis passing through the epicondyles of the femur, wherein the virtual representation of the femur is positioned in a virtual space so that the first axis is parallel with a superior/inferior axis of the pelvis and the second axis is parallel with the coronal plane of the pelvis.

12. The computer-assisted surgery system of claim 9, wherein the processor is configured to establish the first point of reference by:

obtaining computed tomography (CT) data associated with the hip joint;

analyzing a geometric feature of the hip joint based on the CT data; and estimating the center of rotation of the hip joint based on the analysis of the geometric feature.

13. The computer-assisted surgery system of claim 12, wherein the processor is further configured to:

generate a virtual representation of at least a part of the first bone, based on the obtained CT data associated with the hip joint;

capture positions of a plurality of anatomical landmarks associated with the first and second bones; and electronically track a position of the virtual representation of the first bone based on the captured position.

14. The computer-assisted surgery system of claim 13, wherein the processor is further configured to establish the second point of reference by:

capturing a plurality of positions of the virtual representation of the first bone, wherein each of the plurality of positions corresponds to a unique pose of the first bone relative to the second bone; and estimating the post-modification center of rotation of the joint based on the plurality of positions of the virtual representation.

15. The computer-assisted surgery system of claim 13, wherein the processor is further configured to define the first point of reference relative to the virtual representation of the first bone, and wherein approximating the third point of reference includes:

electronically tracking a relative position of the first point of reference relative to the second bone; and determining the third point of reference as the electronically-tracked relative position of the first point of reference when the virtual representation of the first bone is positioned in the predetermined pose.

16. The computer-assisted surgery system of claim 9, wherein the parameter comprises at least one of leg length and offset.

\* \* \* \* \*